United States Patent [19]

DeCote, Jr. et al.

[11] Patent Number: 4,815,017
[45] Date of Patent: Mar. 21, 1989

[54] EGM DATA SAMPLING SYSTEM

[75] Inventors: Robert DeCote, Jr., Miami Beach, Fla.; John H. Livingston, Santa Monica, Calif.

[73] Assignee: Cordis Corporation, Miami, Fla.

[21] Appl. No.: 918,519

[22] Filed: Oct. 14, 1986

[51] Int. Cl.$^4$ ............................................... G06J 1/00
[52] U.S. Cl. ..................................... 364/602; 364/900
[58] Field of Search ............... 364/602, 600, 900, 200, 364/485; 324/379, 384, 99 D; 73/861.77, 117.3

[56] References Cited

U.S. PATENT DOCUMENTS

| | | | |
|---|---|---|---|
| 4,070,709 | 1/1978 | Roberts | 364/602 |
| 4,318,183 | 3/1982 | Byington | 364/900 |
| 4,414,639 | 11/1983 | Telambiras | 364/602 |
| 4,556,067 | 12/1985 | Hokanson | 364/485 |

Primary Examiner—Michael R. Fleming
Attorney, Agent, or Firm—Lockwood, Alex, FitzGibbon & Cummings

[57] ABSTRACT

A digital data system for processing analog electrogram (EGM) signals includes an A/D converter for developing a series of digital data signals (bytes) at a given rate R1. A first whole integer plurality of signals (group N1) is processed for the maximum absolute value thereof. A second whole integer plurality (group N2) is thereafter similarly processed for the maximum absolute value thereof. By alternately outputting each such result, the effective output data stream of the system is at a new sampling rate R2, where $R2 = R1(N1 + N2)/2$. By using more than two groupings, various ratios including non-integer ratios can be implemented.

11 Claims, 3 Drawing Sheets

EGM DATA SAMPLING SYSTEM

BACKGROUND OF THE INVENTION

The present invention relates generally to a method and apparatus for EGM signal display and recording, and more particularly to a system for sampling EGM data. The system is particularly well adapted for use in a pacer system analyzer, which may have a small battery operated plotter of limited slew rate capability.

To assist physicians in treating cardiac disorders of the type for which the use of implantable cardiac pacers is indicated, pacer system analyzers (PSA's) have been developed. These devices are used at the time of pacer implantation to efficiently measure the parameters of a pacer system, including a patient's heart, a pacer to be implanted, and implanted pacer leads, without the need to perform separate procedures requiring multiple interconnections and an undesirably long time period to complete. Pacers to be implanted are tested for proper programming and operation, not only while connected in a simulated pacing system environment, but also while operating in the actual system in which they are to be used. Moreover, pacer system analyzers are preferably equipped to generate pacing pulses as required to support the patient during the pacer implantation, independently of the pacer to be implanted.

By using a pacer system analyzer, a physician is able to adjust the operating parameters of a pacer system as required to suit the specific needs of an individual patient before the pacer has been fully implanted and the implantation surgery completed. This minimizes the need for inconvenient and potentially injurious explantation of the pacer or its associated pacer leads.

One highly desirable function for a pacer system analyzer is to produce a written record of the patient's Electrogram (EGM) signal, as it appears during various stages of the implantation procedure, including paced and unpaced EGM's or before and after adjustments are made to the pacer system. Preferably, this is done by means of a self-contained plotter which provides a facsimile of the desired signal on a strip of paper or other suitable storage medium. From the waveform the attending physician is able to verify and document proper operation of the cardiac system to which the analyzer is connected.

To be suitable for use in a pacer system analyzer it is desirable that a waveform plotter be physically small so as to fit within the analyzer housing, and operable from the internal battery supply of the analyzer so as to not require a separate source of power. Unfortunately, the various plotter assemblies available which meet these requirements have a limited slew rate, or bandpass characteristic, which prevents them from responding to a cardiac signal with sufficient speed to provide a useful and substantially real time display of the signal. The present invention is directed to a data processing system which samples sensed EGM signals to provide digital EGM data point signals useful in providing such a plot.

SUMMARY OF THE INVENTION

The invention is directed to an EGM signal sampling and plotting system. A system for sampling an applied analog signal comprises analog-to-digital conversion means for converting the analog signal to a series of sequential data signals, and a plurality of data storage registers. Means are provided for directing a first predetermined number NI of the data signals to respective ones of the data storage registers, and for computing the maximum absolute value thereof to develop a first data point output signal. Means are further provided for directing a second predetermined number $N_2$ of the data signals to respective ones of the data storage registers, and for computing the maximum absolute value thereof to develop a second data point output signal sequential to the first data point signal, the two signals together providing an effective sampling rate of $$\frac{N_1 + N_2}{2}$$

relative to said sequential data signals.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
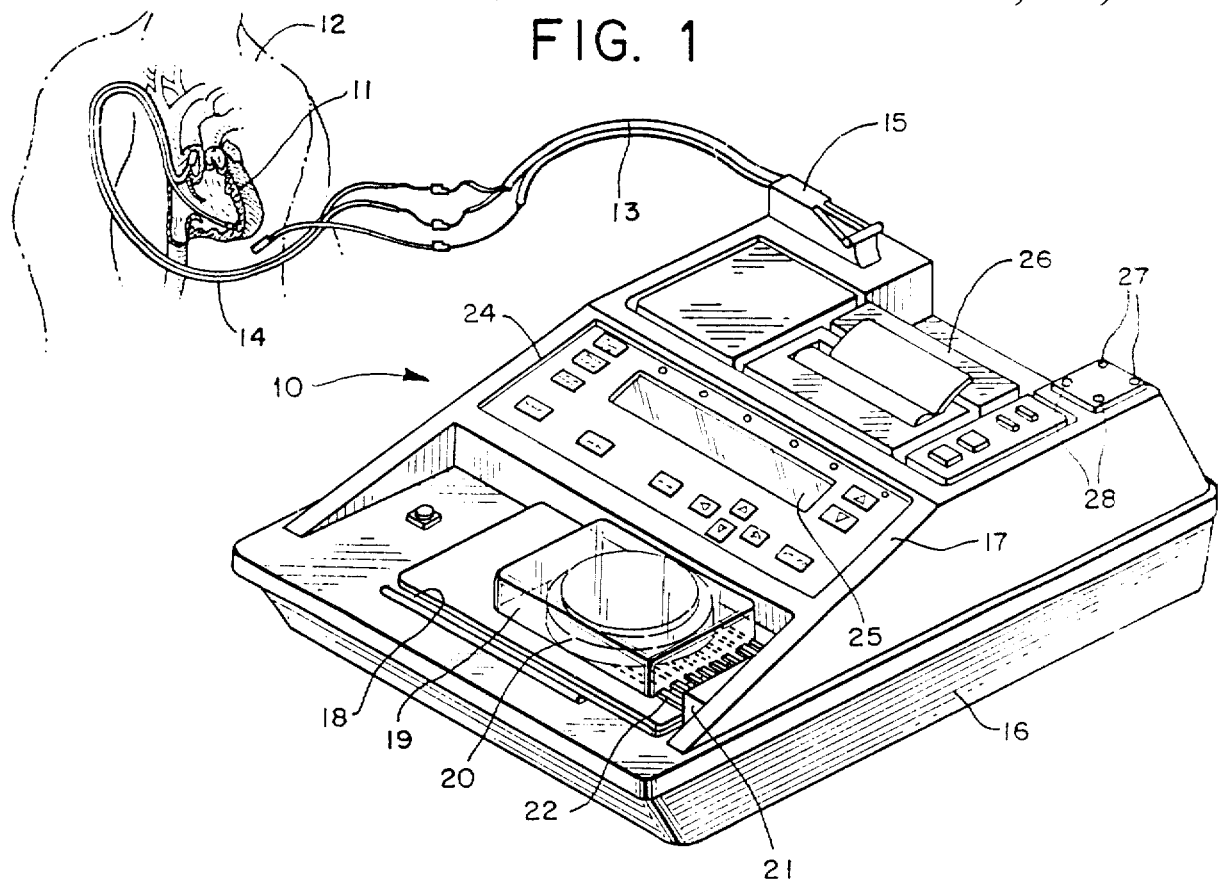
FIG. 1 is a perspective view of a pacer system analyzer incorporating an EGM signal sampling system constructed in accordance with the invention.

Referring to the drawings, and particularly to FIG. 1, a pacer system analyzer 10 is shown which incorporates an EGM plotting system constructed in accordance with the invention. As illustrated, the analyzer 10 is connected to the heart 11 of a patient 12 by means of a pacer lead set 14 and patient cable 13, which may be conventional in construction and operation. The pacer lead set 14 is electrically connected to analyzer 10 by means of a patient cable 13 and a multicontact connector assembly 15.

Pacer system analyzer 10 is contained within a generally rectangular housing 16 formed of a durable, insulating plastic or similar material and includes a sloping, generally flat, control panel 17. A portion of the housing is formed to provide a receptacle 18 for receiving a sealed package 19 containing a sterile implantable cardiac pacer 20. An electrical connector assembly 21 in recess 18 engages an electrical connector assembly 22 on package 19 to provide electrical communication between the analyzer and pacer 20.

Panel 17 includes a plurality of pressure sensitive user-actuable push button controls on keyboard 24 and a liquid crystal display (LCD) 25. PSA 10 operates in one of several user-selected modes in accordance with entered key stroke commands. To assist the user in selecting the appropriate operating mode, a series of internally generated instructions and a plurality of measured pacer system operating parameters are displayed on LCD 25.

A plotter mechanism 26 provides a near real time plot of sensed EGM signals as well as a printed record of measured pacer system operating parameters and measured patient parameters. Two sets o EGM electrodes 27 and 28 provide isolated atrial and ventricular cardiac signals for connection to external instrumentation.

The patient's heart 11, implanted cardiac lead set 14, patient cable 13, and pacer 20 together form a pacer system. Pacer system analyzer 10 functions to automatically measure various parameters of this system and thereby to assist a physician in selecting, implanting and adjusting the pacer system components for maximum effectiveness. Additionally, proper operation of the system can be verified before final implantation, and pacing pulses for supporting the patient during pacer system implantation can be generated.

Figure 2:
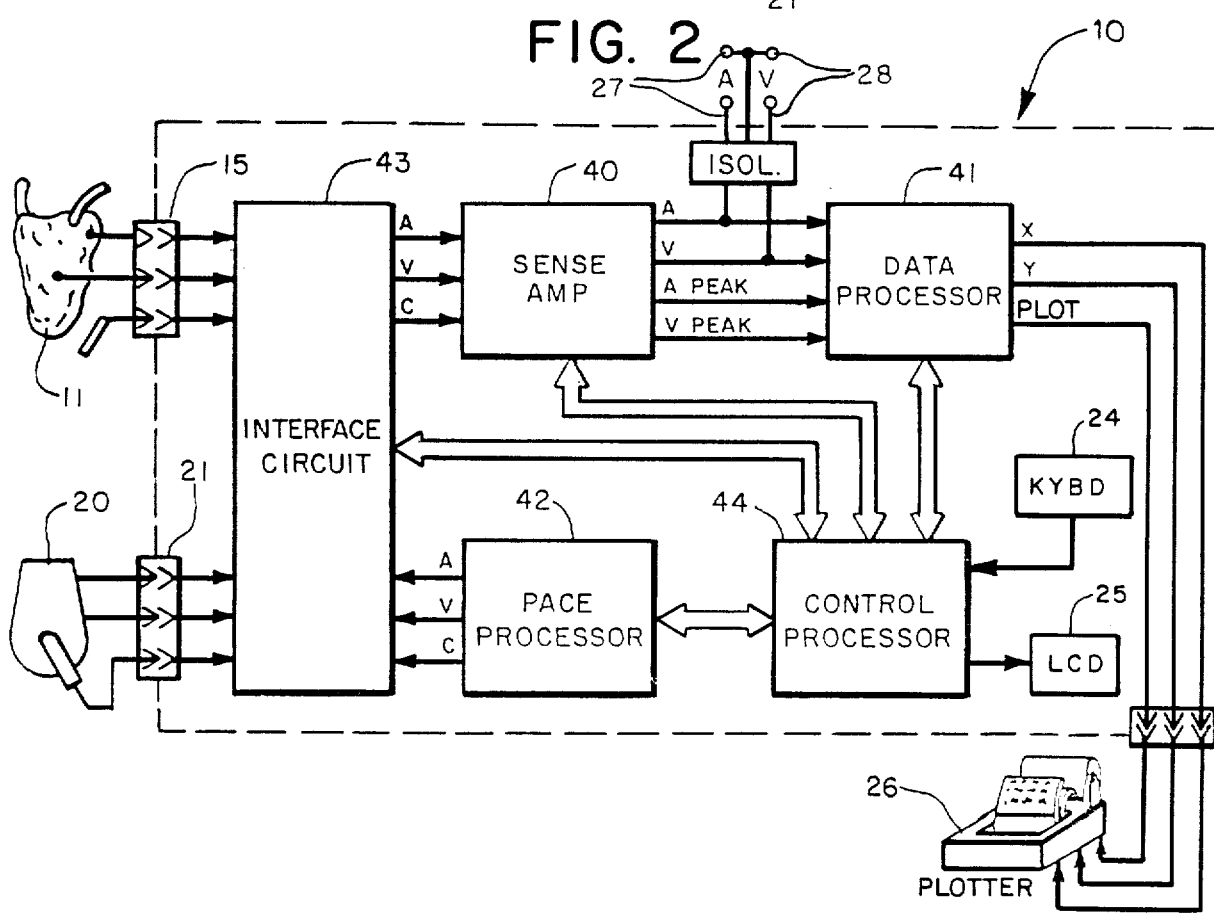
FIG. 2 is a simplified functional block diagram showing the principal components of the pacer system analyzer of FIG. 1.

Referring to the simplified PSA system functional block diagram of FIG. 2, pacer system analyzer 10 includes a sense amplifier 40 for amplifying sensed cardiac signals, a data processor 41 for processing the sensed signals, a pace processor 42 for generating atrial and/or ventricular pacing signals, an interface circuit 43 for coupling the patient's heart 11 and implantable pacer 20 to the pacer system analyzer, and a control processor 44 for controlling the operation of the analyzer components.

Control processor 44 is preferably microprocessor based and is programmed to generate system control signals in response to user-entered keystroke commands from user keyboard 24. Additionally, the control processor may generate a series of user instructions for display on LCD 25.

Pace processor 42 generates pacing pulses for application to the patient's heart 11 to facilitate measurement of patient parameters and to provide basic patient life support. Atrial and ventricular pacing pulses of predetermined amplitude, duration and rate are generated in accordance with applied pace control signals from control processor 44. The pacing pulses are conveyed from the pace processor through interface circuit 43 to the patient heart through pacer lead set 14 and patient cable 13.

As further illustrated in FIG. 2, pacer 20 is connected by connector 21 to interface circuit 43. Upon application of an appropriate control signal from control processor 44, interface circuit 43 couples pacer lead set 14 to pacer 20 whereupon the heart is paced by the pacer. Accordingly, by producing appropriate control signals, the control processor 44 can cause the heart to be paced by either pace processor 42 or by implantable pacer 20.

Atrial and/or ventricular intracardiac signals impinging upon pacer lead set 14 are applied to respective inputs of sense amplifier 40. The sense amplifier generates atrial and/or ventricular strobe signals for application to control processor 44 upon the occurrence of atrial or ventricular intracardiac signals above a predetermined threshold. Additionally, the sense amplifier provides amplified atrial and ventricular signals for application to data processor 41 and for application to EGM terminal pairs 27 and 28 through an isolation circuit, as well as signals indicative of the peak atrial and ventricular R-waves sensed by pacer lead set 14. Data processor 41 performs the mathematical operations required to calculate various patient or pacer system operating parameters for display on LCD 25 or for printing by plotter 26.

Figure 3:
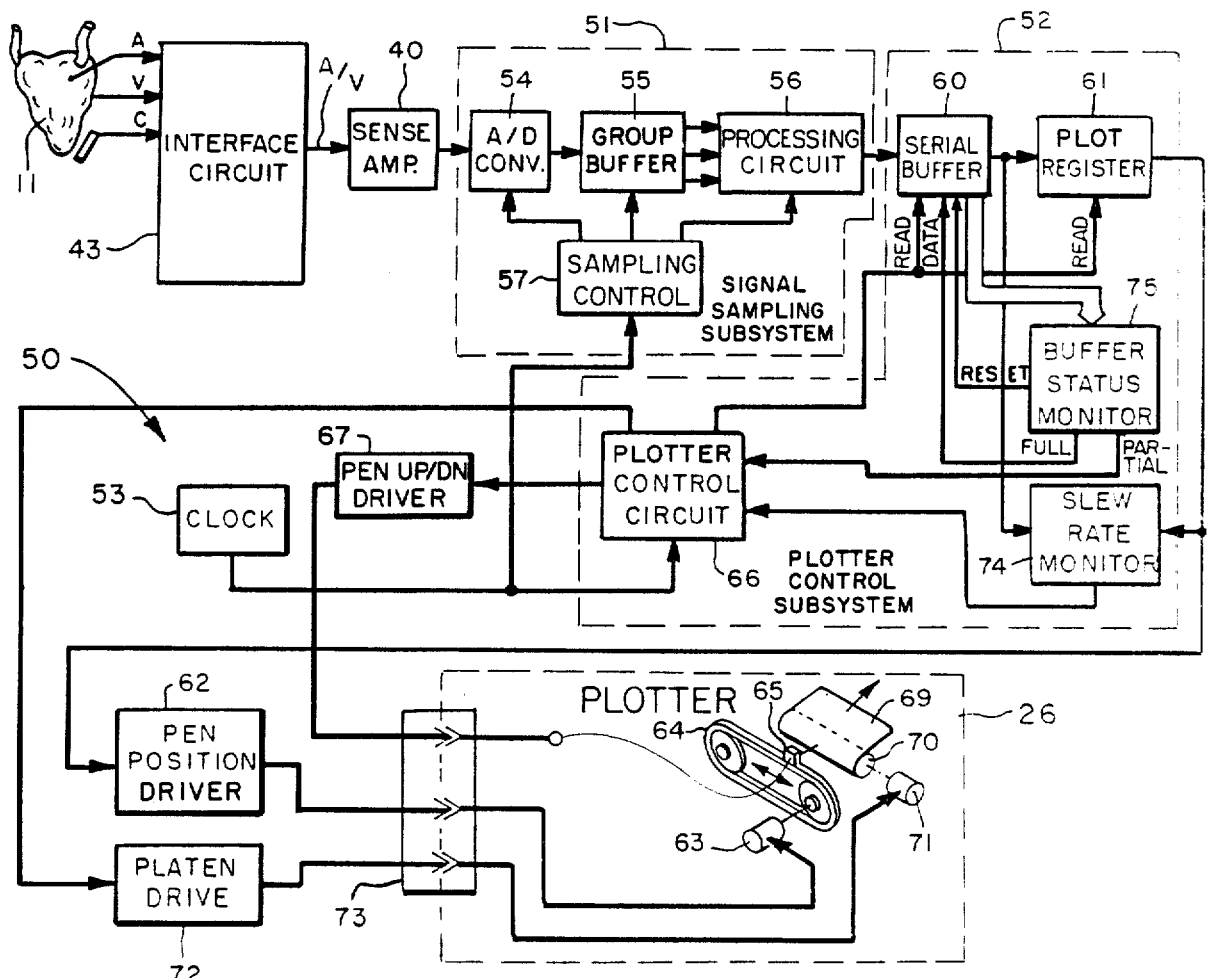
FIG. 3 is a simplified functional block diagram of the EGM data sampling and plotting systems of the pacer system analyzer.

Referring to FIG. 3, pacer system analyzer 10 includes a plotting system 50 which enables plotter 26 to accurately plot in near real time cardiac signals sensed by pacer lead set 14. This system includes an EGM sampling subsystem 51, wherein the sensed cardiac signal as amplified by sense amplifier 40 is periodically sampled to develop a series of digital data signals (bytes), and a plotter control subsystem 52, wherein the data signals are processed prior to application to plotter 26. The two subsystems 51 and 52, operating in synchronism under control of a clock circuit 53, allow plotter 26 to maintain essential EGM waveform morphology for diagnostic and evaluative purposes while plotting the EGM data in near real time on a plotter which has a bandpass or slew rate characteristic substantially lower than that of the signal to be plotted. One construction of plotter control system 52 which has proven particularly advantageous for use in the present application is described in the copending application of the present inventor entitled "EGM Plotting System for Use With Slew-Rate Limited Plotter", Ser. No. 918,535, filed concurrently herewith.

Referring to FIG. 3, the EGM data sampling and processing subsystem 51 includes, in accordance with the invention, at the output of sense amplifier 40, an analog-to-digital converter 54 which converts the amplified analog sense signal from amplifier 40 to a series of digital bytes with values which correspond to signal amplitude. Predetermined numbers of these serially occurring digital signals are temporarily stored in a group buffer circuit 55 which provides a memory location for each signal of the group. Immediately after each group of data bytes is stored in group buffer 55, processing circuit 56 selects the maximum absolute value of the bytes within that group. Since the occurrence rate of the group processed signal is lower than that (R1) at the output of the analog-to-digital converter, a lower data rate (R2) is presented to the plotter control circuit 52. However, since a relatively small number of digital data signals comprise each group, and the repetition rate of the group data signals is relatively high, EGM waveform morphology is essentially maintained.

Thus, subsystem 51 is for the purpose of systematically converting the high incoming data rate, R1, into the slower derived effective plotting rate, R2. System operation is such that R1/R2 need not be a whole number. Subsystem 52 is for the purpose of controlling paper speed in such manner that real time slew rates considerably higher than what the plotter can follow in real time may be plotted.

The operation of A/D converter 54, group buffer 55 and data processing circuit 56 are under the control of a data sampling control circuit 57 which may be constructed to provide a variety of different sampling rates. In the present application, it has been found advantageous to sample the EGM data 2.5 times more often that it is plotted. To achieve this effective sampling rate, the data sampling control circuit 57 causes two data points to be first accumulated in group buffer 55, and the maximum absolute value of these two points to be determined and transferred to plotter control system 52. Group buffer 55 is then cleared, and data sampling control circuit 57 then causes three data points to be taken and stored in group buffer 55. The maximum absolute value of these three points is determined, and the change between this value and the previous group output value is transferred to plotter control system 52. When the cycle is repeated for two data points, three data points, two data points, three data points etc., the desired effective 2.5:1 sampling ratio is obtained.

Within the plotter control circuit 52 the serially occurring group-processed data bytes are applied to a conventional serial data buffer 60, wherein they queue in a first-in first-out manner. The output of serial buffer 60 is applied to momentary storage means in the form of a plot register 61 which stores the digital buffer output signal for application to plotter 26 in response to an applied command signal. Thus, the data point signal stored in register 61 is the data point presently being plotted, and the data point signal appearing at the output of serial buffer 60 is the next data point to be plotted.

The output of plot register 61 is applied to a pen position drive circuit 62, which operates in conjunction with a pen positioning stepper motor 63 and associated pen positioning mechanism 64 to position a writing pen 65 in a manner well known to the art.

Operation of pen 65 is under the control of a plotter control circuit 66, which provides an actuating signal to the pen through an amplifier 67 when the pen and the print paper 69 are properly positioned. Positioning of the print paper is accomplished by a platen 70 of conventional construction, which is driven by actuator means in the form of a stepper motor 71. The operation of stepper motor 71 is controlled by a platen drive circuit 72, which operates in accordance with control inputs provided by plotter control circuit 66. A connector 73 allows the plotter 26, which may be conventional in construction and operation, and which may, for example, be that commercially available as the Model PC916TE manufactured by Quasar to be readily removed for service and adjustment.

To overcome the slew rate limitation of plotter 26, plotter control system 52 includes means for varying the paper feed rate of the plotter in accordance with the slew rate of data being processed. In particular, plotter system 52 includes slew rate detection means in the form of a slew rate monitor circuit 74 which compares the value of the data point signal stored in register 61 for plotting with the value of the data point at the output of serial buffer 60, next to be plotted. The difference between these two values divided by the time per plotted point constitutes the slew rate of the next data point signal to be plotted. This difference signal is applied to plotter control circuit 66, which varies the operating rate of the platen drive motor 71, and hence the rate of advance of the paper 69, to accommodate the slew rate of the data being printed. In this way, the paper is slowed, allowing more time for the positioning of pen 65 when a larger pen excursion is required by a high slew rate, and the paper is speeded, allowing less time for pen positioning when only a small excursion is required by a small slew rate.

After each data point is plotted a new data point enters register 61 and a new paper drive rate is calculated, and the pen is advanced to a position according to the then present ΔX signal as the platen advances the paper at the calculated paper speed. After the data point has been plotted, the plot register is loaded with another new data point signal (ΔX) from serial buffer 60. The procedure continues, the paper speed being alternately increased and decreased as required to accommodate variations in slew rate ΔX and the status of serial buffer 60.

When the period of time between the plotting of grouped data points by pen 65 is greater than the repetition rate of data point signals applied to serial buffer 60 by sampling system 51, as during high slew rate periods accompanying cardiac events, the serially occurring group data point signals queue in first-in first-out order in serial buffer 60. To reduce the number of data point signals thus queued, after the high slew rate, short duration, condition has abated, as during the relatively long cardiac rest periods, the operating rate of taper drive motor 71, and hence the paper speed data point signals queue in first-in first-out order in serial buffer 60. To reduce the number of data point signals thus queued, after the high slew rate, short duration, condition has abated, as during the relatively long cardiac rest periods, the operating rate of taper drive motor 71, and hence the paper speed of the plotter, is increased above the rate at which group data point signals are generated by data sampling stage 51. To this end, the presence of queued group data point signals in serial buffer 60 is monitored by a buffer status monitor circuit 75.

When multiple group data point signals are present in the buffer, indicating that the plotter is running behind the production of data by sampling system 51, an output signal is developed which causes plotter control circuit 66 to operate stepper motor 71 at an increased rate greater than the rate of the incoming group data point signals, provided that the slew rate of the next to be plotted data does not exceed the capability of the plotter. If the slew rate does exceed plotter capability then the plotter continues to operate at a reduced paper speed to accommodate the higher slew rate, and digital data point signals continue to queue in serial buffer 60. In the event that an overflow condition is reached, i.e., serial buffer 60 becomes completely occupied with group processed digital data point signals and additional signals cannot be accommodated, the buffer status monitor 75 resets the serial buffer 60, clearing it of all data. The paper speed is increased while the reset line to the serial buffer remains high for a predetermined time interval. Meanwhile, a "break protocol" set of instructions is given to the plotter. For example, the pen may be simply lifted from the paper for a blank interval, or a set of timing marks can be placed on the plot's baseline, providing the user with an unmistakable break indication, a baseline indication, and a time scale "ruler". Immediately thereafter, the system resumes its plotting routines as described above.

In practice, plotter 26 is provided with an ample opportunity to catch up with data provided by sampling system 51 by reason of the comparatively long refractory periods which appear in the cardiac signal between successive cardiac events.

Synchronism between the data sampling system 51 and the plotter control system 52 is provided by clock circuit 53, which provides clock pulses to the data sampling control circuit 57 of system 51 and to the plotter control circuit 66 of system 52. This assures that the entry of data point signals into serial buffer 60 will not interfere with the reading out of signals from the buffer into plot register 61.

Figure 4:
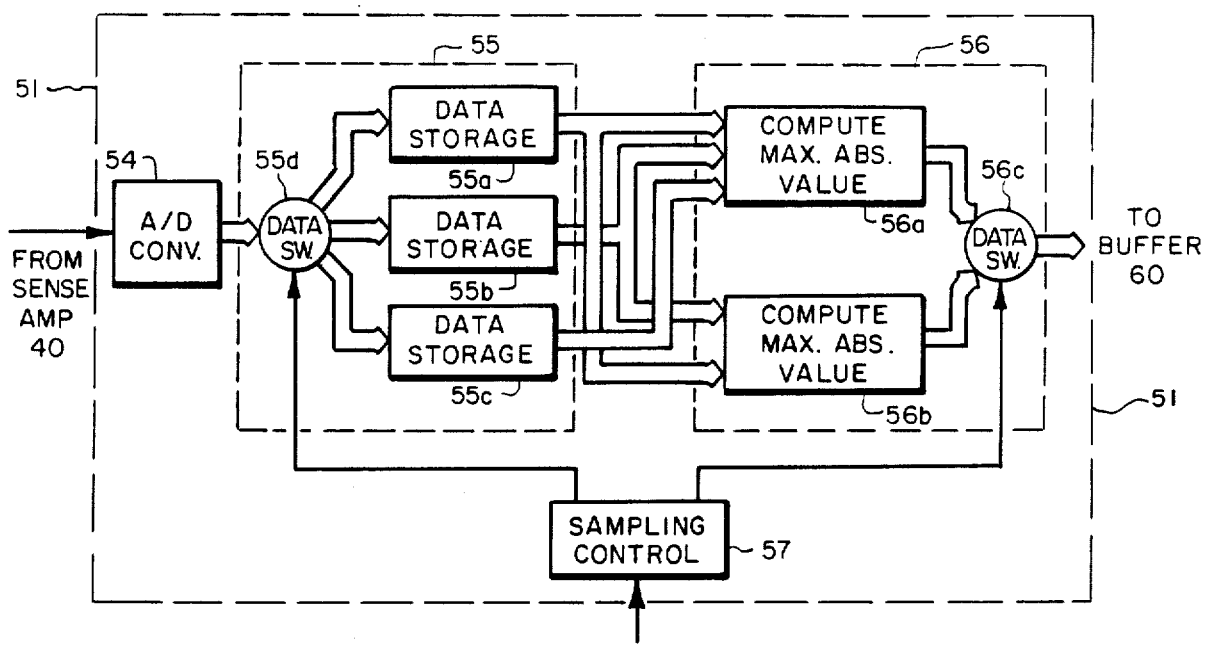
FIG. 4 is an expanded functional block diagram of the EGM signal sampling system of the invention.

Referring to FIG. 4, in a preferred construction of the EGM sampling system 51 for providing a 2.5 to 1 sampling rate, the output of analog-to-digital converter 54 is applied to three data storage registers 55a–55c through a data switch 55d. In operation, the sequentially-occurring digital bytes are entered in-sequence to respective ones of the three registers, the first signal to register 55a, then the next to register 55b, and the next to register 55c. After three signals have been thus entered, a computing circuit 56a determines the maximum absolute value of the three signals, and this value with its sign is conveyed as a first group data point signal to serial buffer 60 through data switch 56c.

A second data point signal is no developed by entering two sequentially-occurring data signals from converter 54 to data storage registers 55a and 55b. A computing circuit 56b then determines the maximum absolute value of these two signals, and this value with its sign is conveyed as a second group data point signal to serial buffer 60 thru data switch 56c.

Since the first data point signal represents a sampling of three data signals, and the second data point signal represents a sampling of two data signals, the two sequentially-occurring group data point signals digital bytes are entered in-sequence to respective ones of the three registers, the first signal to register 55a, then the next to register 55b, and the next to register 55c. After three signals have been thus entered, a computing circuit 56a determines the maximum absolute value of the three signals, and this value with its sign is conveyed as a first group data point signal to serial buffer 60 through data switch 56c.

A second data point signal is now developed by entering two sequentially-occurring data signals from converter 54 to data storage registers 55a and 55b. A computing circuit 56b then determines the maximum absolute value of these two signals, and this value with its sign is conveyed as a second group data point signal to serial buffer 60 thru data switch 56c.

Since the first data point signal represents a sampling of three data signals, and the second data point signal represents a sampling of two data signals, the two sequentially-occurring group data point signals continuously repeated provides an effective 2.5-to-1 sampling rate relative to the EGM data signals. This makes possible the plotting or recording of sensed EGM or EKG data which would otherwise not be possible because of excessive slew rates.

Other effective sampling rates are possible by varying the number of data signals grouped and processed in each cycle. Where the maximum absolute value of $N_1$ data signals are determined in the first grouping cycle, and the absolute maximum value of $N_2$ data signals are determined in the second grouping cycle, the effective sampling rate S for two repetitive cycles can be expressed as $$S = \left( \frac{N_1 + N_2}{2} \right)$$

Where more than two repetitive cycles are provided, for n cycles the sampling rate can be expressed $$S = \left( \frac{N_1 + N_2 + \ldots + N_K}{K} \right)$$

For the battery-operated plotter utilized in the present embodiment, a nominal plotting speed of 10 millimeters per second has been found to provide good results. At this nominal speed, the platen stepper motor 71 provides a paper advance of 0.2 millimeters per step and each step requires 20 milliseconds for completion. The pen can move 50 millimeters per second, or 260 steps per second. Consequently, while the paper moves (Y axis) one step, the pen can advance (X axis) 5 steps. Consequently, a pen deflection (X) of five steps, or 1 millimeter, can be accommodated by plotter 26 when operating at a nominal print rate. To respond to signals having a higher slew rate it is necessary that the platen stepper motor 71 be slowed to allow more time for pen repositioning.

While the sampling rate may vary in individual applications, it has been found advantageous to sample and store the incoming cardiac signal at a rate of 8 milliseconds per byte. However, plotting is being accomplished at a nominal rate of 20 milliseconds per step, making the incoming rate 2.5 times the plotting rate. To properly accommodate the sampling rate to the plotting rate it is necessary to apply a 2.5 division factor to the incoming data. To this end, the incoming data stream is divided into groups of alternately two bytes and three bytes each. Each such group is examined for the largest absolute value in the group. The largest absolute value constitutes the digital data point signal supplied to serial buffer 60 of plotter system 52. While this sampling technique does introduce some loss of detail and distortion, the most salient features of the EGM will be retained.

It will be further appreciated that other sampling rates may require other division factors, and the sampling technique may be adjusted accordingly. It will be appreciated that the EKG data sampling system of the invention can be implemented within a conventional microprocessor by means of known conventional programming techniques. For example, within pacer system analyzer 10, the sampling system can be implemented within data processor 41, which may comprise a conventional microprocessor.

Figure 5:
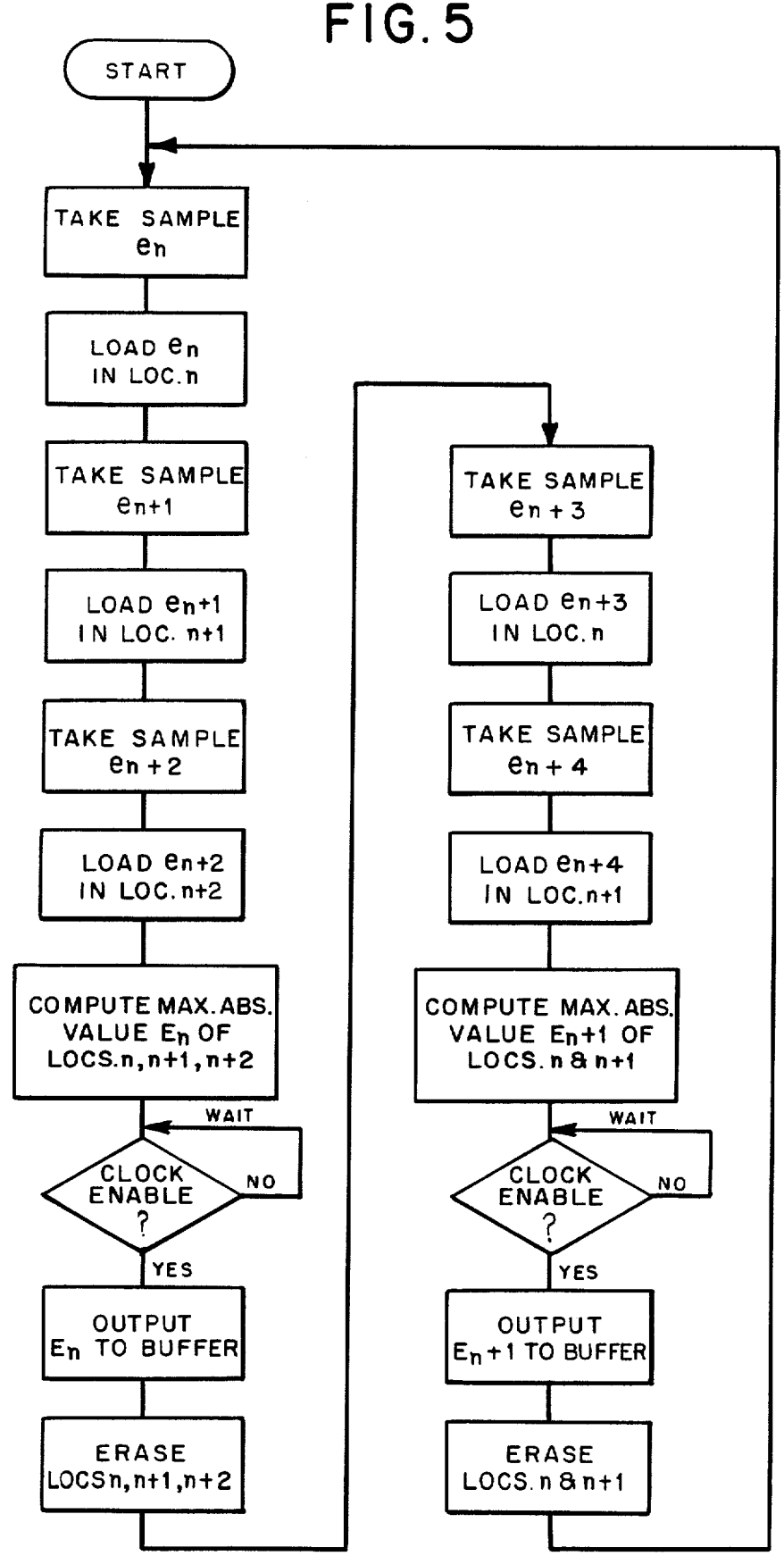
FIG. 5 is a simplified flow chart illustrating the method of operation of the EGM signal processing system of the invention.

The microprocessor-based implementation of the EGM data sampling system can be structured as shown by the simplified flow chart of FIG. 5. Upon operator initiation of a plot routine, a data processing subroutine is followed wherein data is sampled first to find the largest absolute value of three successive points, and then to find the largest absolute value of the next two successive points. This group processing action results in reduced data rate byte stream flowing into the first in-first out data buffer the action of which has been described in copending application of the present inventor entitled "EGM Plotting System for Use With Slew-Rate Limited Plotter", Ser. No. 918,535 filed concurrently herewith.

While the plotting system of the invention has been shown in conjunction with a pacer system analyzer, it will be appreciated that the system may be utilized in virtually any monitoring and recording application wherein plotters or data recorders of limited slew rate capability are employed and the nature of the signal to be plotted is such as to allow "catch-up" processing to be implemented. Furthermore, the data sampling rates in a particular application may vary as a function of the characteristics of the plotter, the capacity of the buffer, the nature and range of slew rates of the data, and various other variables in the application.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A system for sampling an applied analog signal, comprising:
   analog-to-digital conversion means for converting the applied analog signal to a series of sequentially occurring data signals each of predetermined finite duration;
   first and second digital data storage means;
   means for directing a predetermined whole integer plurality $N_1$ of said sequentially occurring date signals to said first data storage means;
   means for computing the maximum absolute value of said $N_1$ data signals in said first data storage means to develop a first digital data point output signal $X_1$;
   means for directing a predetermined whole integer plurality $N_2$ of said sequentially occurring data signals immediately following said first plurality $N_1$ of sequentially occurring data signals to said second data storage means;
   means for computing the maximum absolute value of the data signals in said second data storage means to develop a second digital data point signal $X_2$; and
   means for producing an output signal sequentially comprising said first and second digital data point signals $X_1$ and $X_2$ whereby the applied analog signal is sampled at a rate $$\frac{N_1 + N_2}{2}$$

2. A data sampling system as defined in claim 1 wherein said whole integer plurality $N_2$ is less than said whole integer plurality $N_1$.

3. A data sampling system as defined in claim 2 wherein said whole integer plurality $N_1$ is 3 and said whole integer plurality $N_2$ is 2, and said effective sampling rate is 2.5.

4. A data sampling system as defined in claim 2 wherein said first digital data storage means comprises a plurality $N_1$ of digital data storage registers.

5. A data sampling system as defined in claim 4 wherein said second digital data storage means comprises a portion of said plurality $N_1$ of digital data storage registers, and said second plurality $N_2$ of said sequentially occurring data point signals are stored in respective ones of said portion of said storage.

6. A data sampling system as defined in claim 1 wherein said first and second digital data storage means comprise a RAM.

7. The method of sampling an applied analog signal, comprising:
   converting the analog signal to a series of sequentially occurring data signals each of predetermined finite duration;
   directing a predetermined whole number $N_1$ of said sequentially occurring data signals to a first digital data storage means;
   computing the maximum absolute value of said $N_1$ data signals in said first digital data storage means to develop a first digital data point output signal $X_1$ of predetermined finite duration;
   directing a predetermined plurality $N_2$ of said sequentially occurring digital data signals immediately following said first plurality $N_1$ of sequentially occurring digital data signals to a second digital data storage means;
   computing the maximum absolute value of the data signals in said second data storage means to develop a second digital data point signal $X_2$ of finite duration; and
   producing an output signal sequentially comprising said first and second digital data point signals $X_1$ and $X_2$ whereby the applied analog signal is sampled at a rate $$\frac{N_1 + N_2}{2}$$

8. The sampling method as defined in claim 7 wherein said whole integer plurality $N_2$ is less than said whole integer plurality $N_1$.

9. The sampling method defined in claim 8 wherein said whole integer plurality $N_1$ is 3 and said whole integer plurality $N_2$ is 2, and said effective sampling rate is 2.5.

10. The sampling method defined in claim 8 wherein said first digital data storage means comprises a plurality $N_1$ of digital data storage registers.

11. The sampling method as defined in claim 10 wherein said second digital data storage means comprises a portion of said plurality $N_1$ of digital data storage registers, and said second plurality $N_2$ of said sequentially occurring data point signals are stored in respective ones of said portion of said storage.

* * * * *